US007208272B2

(12) United States Patent
Lee et al.

(10) Patent No.: US 7,208,272 B2
(45) Date of Patent: Apr. 24, 2007

(54) MULTIPLEX PCR PRIMER SET FOR HUMAN HNF-1α GENE AMPLIFICATION

(75) Inventors: Yeon-su Lee, Gyeonggi-do (KR); Mi-kyung Kim, Daejeon (KR); Jung-nam Lee, Daejeon (KR)

(73) Assignee: Samsung Electronics Co., Ltd. (KR)

( * ) Notice: Subject to any disclaimer, the term of this patent is extended or adjusted under 35 U.S.C. 154(b) by 208 days.

(21) Appl. No.: 10/320,095

(22) Filed: Dec. 16, 2002

(65) Prior Publication Data

US 2003/0149258 A1    Aug. 7, 2003

(30) Foreign Application Priority Data

Dec. 18, 2001    (KR) ............................... 2001-80909

(51) Int. Cl.
  *C12Q 1/68* (2006.01)
  *C12D 19/34* (2006.01)
  *C07H 21/02* (2006.01)
  *C07H 21/04* (2006.01)

(52) U.S. Cl. .................. 435/6; 435/91.2; 536/23.1; 536/24.3; 536/24.33

(58) Field of Classification Search .................... 435/6, 435/91.1, 91.2; 536/23.1, 24.3
See application file for complete search history.

(56) References Cited

U.S. PATENT DOCUMENTS

| 4,683,195 | A |   | 7/1987  | Mullis et al. ................ 435/6    |
|-----------|---|---|---------|----------------------------------------|
| 4,683,202 | A |   | 7/1987  | Mullis ........................... 435/91 |
| 4,800,159 | A |   | 1/1989  | Mullis et al. ............ 435/172.3    |
| 5,480,784 | A | * | 1/1996  | Kacian et al. ............ 435/91.21   |
| 5,541,060 | A |   | 7/1996  | Bell et al. ....................... 435/6 |
| 5,582,989 | A |   | 12/1996 | Caskey et al. .................. 435/6  |
| 6,187,533 | B1|   | 2/2001  | Bell et al. ...................... 435/6 |

FOREIGN PATENT DOCUMENTS

| EP | 0 682 120 A1 | 11/1995 |
|----|--------------|---------|
| WO | WO 89/01050  | 2/1989  |
| WO | WO 93/21343  | 10/1993 |
| WO | WO 98/11254  | 3/1998  |

OTHER PUBLICATIONS

Buck, G.A., et al., "Design Strategies and Performance of Custom DNA sequencing Primers", Biotechniques, vol. 27, pp. 528-536 (1999).*

Drobyshev, A. et al., "Sequence analysis by hybridization with oligonucleotide mirochip: identification of beta-thalassemia mutations", Gene, vol. 188, pp. 45-52 (1997).*

Froguel, P. et al., "Genetic Determinants of Type 2 Diabetes", Rec. Prog. Hormone Res., vol. 56, pp. 91-105 (2001).*

Fletcher, B. et al., "Risk Factors for Type 2 Diabetes Mellitus", J. Cardiovasc. Nursing, vol. 16, pp. 17-23 (2002).*

Cuppens, H. et al., "Simultaneous screening for 11 mutations in the cystic fibrosis transmembrane conductance regulator gene by multiplex amplification and reverse dot-blot", Mol. Cell. Probes, vol. 6, pp. 33-39 (1992).*

Fuscoe, J. C. et al. "Detection of Deletion Mutations Extending Beyond the HPRT Gene by Multiplex PCR Analysis", Somatic Cell and Mol. Gen., vol. 20, pp. 39-46 (1994).*

Wang, D.G. et al., "Large-Scale Identification, Mapping, and Genotyping of Single-Nucleotide Polymorphisms in the Human Genome", Science, vol. 280, pp. 1077-1082 (1998).*

"Primer-Directed Enzymatic Amplification of DNA with a Thermostable DNA Polymerase"; Authors: Randall K. Saiki, David H. Gelfand, Susanne Stoffel, Stephen J. Scharf, Russell Higuchi, Glenn T. Horn, Kary B. Mullis and Henry A. Erlich; Reports, Science, vol. 239; pp. 487-491; Jan. 29, 1988.

"Identification of nine novel mutations in the hepatocyte nuclear factor 1 alpha gene associated with maturity-onset diabetes of the young (MODY3)"; Authors: Martine Vaxillaire, et al.; Oxford University Press; Human Molecular Genetics, vol. 6, No. 4; 1997; pp. 583-586.

"Mutations in the Hepatocyte Nuclear Factor-1α Gene in MODY and Early-Onset NIDDM—Evidence for a Mutational Hotspot in Exon 4"; Authors: Pamela J. Kaisaki, et al., Diabetes, vol. 46; Mar. 1997; pp. 528-535.

Mutations in the hepatocyte nuclear factor-1α gene in maturity-onset diabetes of the young (MODY3); Authors; Kazuya Yamagata, et al.; Letters to Nature, vol. 384 Dec. 5, 1996; pp. 455-458.

European Partial Search Report; European Application No. EP 02 02 8140; Date: Oct. 24, 2003.

* cited by examiner

Primary Examiner—Teresa E. Strzelecka
(74) Attorney, Agent, or Firm—Cantor Colburn LLP

(57) ABSTRACT

A primer pool for amplifying a target sequence of a human HNF-1α gene, including at least one set of primers or variant primers thereof, each set of primers being identified by two consecutive SEQ ID NOS, the SEQ ID NOS being given as from SEQ ID NO.3 to SEQ ID NO.22, is provided. A target sequence such as the human HNF-1α gene may be amplified with a high specificity, a high speed, a high sensitivity and a low cost through a multiplex PCR to detect a maturity-onset of diabetes of the young (MODY) 3 associated gene.

18 Claims, 4 Drawing Sheets

Fig.4

```
Promoter   1 CTCCTGTCTCAGCATGATGCCCCTACAAGGTTCTTTCGGGGGTGGGACCCAACGCTGCTC
Query     73 CTCCTGTCTCAGCATGATGCCCCTACAAGGTTCTTTCGGGGGTGGGACCCAACGCTGCTC Promoter  61 TCCTGATGGCCTCCCTGGCTCCCAGCACCTTCCATCCCAGCTGCTCAGGGCCCCTCACCT
Query    133 TCCTGATGGCCTCCCTGGCTCCCAGCACCTTCCATCCCAGCTGCTCAGGGCCCCTCACCT Promoter 121 GCGCCTCCCCCACCCTCCCCTCTGCCCACTCCCATCGCAGGCCATAGCTCCCTGTCCCTC
Query    193 GCGCCTCCCCCACCCTCCCCTCTGCCCACTCCCATCGCAGGCCATAGCTCCCTGTCCCTC Promoter 181 TCCGCTGCCATGAGGCCTGCACTTTGCAGGGCTGAAGTCCAAAGTTCAGTCCCTTCGCTA
Query    253 TCCGCTGCCATGAGGCCTGCACTTTGCAGGGCTGAAGTCCAAAGTTCAGTCCCTTCGCTA Promoter 241 AGCACACGGATAAATATGAACCTTGGAGAATTTCCCCAGCTCCAATGTAAACAGAACAGG
Query    313 AGCACACGGATAAATATGAACCTTGGAGAATTTCCCCAGCTCCAATGTAAACAGAACAGG Promoter 301 CAGGGGCCCTGATTCACGGGCCGCTGGGGCCAGGGTTGGGGGTTGGGGGTGCCCACAGGG
Query    373 CAGGGGCCCTGATTCACGGGCCGCTGGGGCCAGGGTTGGGGGTTGGGGGTGCCCACAGGG Promoter 361 CTTGGCTAGTGGGGTTTTGGGGGGGCAGTGGGTGCAAGGAGTTTGGTTTGTGTCTGCCGG
Query    433 CTTGGCTAGTGGGGTTTTGGGGGGGCAGTGGGTGCAAGGAGTTTGGTTTGTGTCTGCCGG Promoter 421 CCGGCAGGCAAACG
Query    493 CCGGCAGGCAAACG
```

MULTIPLEX PCR PRIMER SET FOR HUMAN HNF-1α GENE AMPLIFICATION

FIELD OF THE INVENTION

The present invention relates to a primer pool for amplifying a human HNF-1α gene, and more particularly, to a primer pool for amplifying a target DNA sequence in a human HNF-1α gene by multiplex PCR.

BACKGROUND OF THE INVENTION

One type of process utilized for the detection of hybridized nucleic acids involves polymerase chain reaction (PCR). The PCR process is well known in the art (U.S. Pat. Nos. 4,683,195, 4,683,202 and 4,800,159). In PCR, nucleic acid primers that are complementary to opposite strands of a nucleic acid amplification target sequence are permitted to anneal to the denatured sample. Next, DNA polymerase (typically heat stable) extends the DNA duplex from the hybridized primer. The process is then repeated to amplify the nucleic acid target. If the nucleic acid primers do not hybridize to the sample, then there is no corresponding amplified PCR product. In this case, the PCR primer acts as a hybridization probe.

In a PCR method, the amplified nucleic acid product may be detected in a number of ways, e.g., by incorporation of a labeled nucleotide into the amplified strand by using labeled primers. Primers used in PCR include, but are not limited to radioactive substances, fluorescent dyes, digoxygenin, horseradish peroxidase, alkaline phosphatase, acridinium esters, biotin and jack bean urease. PCR products made with unlabeled primers may be detected in other ways, such as electrophoretic gel separation followed by dye-based visualization.

PCR-based methods are of limited use for the detection of nucleic acids of unknown sequence. The human genome is composed of about $3 \times 10^9$ nucleotides; thus, it is difficult to isolate and analyze a specific human gene. Yet, PCR can amplify a target sequence with high speed, specificity and sensitivity by using a set of primers including primers complementary to both ends of the target sequence (Saiki et al. Science 239: 487,1988).

PCR may be widely used in analyzing a disease-associated gene. Specifically, gene amplification by PCR may be useful for analyzing genetic variations of a disease-associated gene in the medical field. A specific disease-associated gene may be amplified using PCR, and analyzed by using a sequencing, hybridization or single strand conformational polymorphism. In analyzing genetic variations of a gene a single PCR may be enough to amplify the entire gene if the size of a target gene is small. However, if the size of a target gene is large, e.g., 1 kb or more, a single PCR may have difficulty in amplifying the entire gene. Thus, PCR may be conducted several times on several portions of the entire gene to amplify the entire gene of a large target gene. In analyzing a genetic variation of a disease-associated gene, a multiple PCR is more frequently used than a single PCR since most disease-associated genes may be 1.5 kb or larger in size.

A multiple PCR process requires a large amount of a sample, for example, a patient's DNA or blood. A multiple PCR also costs more and requires more effort and time. Thus, multiplex PCR assays have been developed to solve the above problems. A multiplex PCR simultaneously amplifies a plurality of target sequences of a gene in one reaction. Therefore, a plurality of target sequences are amplified by a single PCR using a primer pool for amplifying each target sequence.

Multiplex PCR assays are well known in the art. For example, U.S. Pat. No. 5,582,989 discloses the simultaneous detection of multiple known DNA sequence deletions. The technique disclosed therein uses a first set of probes to hybridize to the targets. Those probes are extended if the targets are present. The extension products are amplified using PCR.

A set of primers for a multiplex PCR may be able to specifically bind to a target sequence and should not interfere with each other in order to amplify the target sequence by a sufficient amount. A multiplex PCR using such a set of primers may be able to save time, effort and cost for amplifying a target sequence in comparison with a single PCR. In analyzing a genetic variation of a gene by using a DNA chip, a multiplex PCR may be useful in amplifying more than one kind of DNA sample in a reaction. Such a DNA chip may be useful in analyzing genetic variations in a gene.

It is known that a genetic variation of a human HNF-1α (hepatocyte nuclear factor-1α) gene, including a point mutation, causes maturity-onset diabetes in the young (MODY 3) (Matschinsky & Magnuson, in 'Molecular Pathogenesis of MODYs', Karqer, 1998; U.S. Pat. No. 5.541,060; WO9321343). MODY 3, a kind of MODY disease (MODY 1, 2, 3, 4 and 5) accounts for about 10–30% of all type II diabetes mellitus cases. Thus, in analyzing a genetic variation of a human HNF-1α gene, it is possible to anticipate a person's propensity to a diabetes mellitus. Therefore, in order to rapidly analyze a human HNF-1α gene using, for example, a DNA chip, a set of primers for amplifying a human HNF-1α gene by a multiplex PCR needs to be developed.

SUMMARY OF THE INVENTION

One of the embodiments of the present invention provides a primer pool comprising at least one set of primers for amplifying at least one target sequence of a human HNF-1α gene, the at least one set of primers being selected from the group consisting of:

(a) a set of primers comprising an oligonucleotide having a sequence given herein as SEQ ID NO. 3 or a variant oligonucleotide thereof and an oligonucleotide having a sequence given herein as SEQ ID NO. 4 or a variant oligonucleotide thereof;

(b) a set of primers comprising an oligonucleotide having a sequence given herein as SEQ ID NO. 5 or a variant oligonucleotide thereof and an oligonucleotide having a sequence given herein as SEQ ID NO. 6 or a variant oligonucleotide thereof;

(c) a set of primers comprising an oligonucleotide having a sequence given herein as SEQ ID NO. 7 or a variant oligonucleotide thereof and an oligonucleotide having a sequence given herein as SEQ ID NO. 8 or a variant oligonucleotide thereof;

(d) a set of primers comprising an oligonucleotide having a sequence given herein as SEQ ID NO. 9 or a variant oligonucleotide thereof and an oligonucleotide having a sequence given herein as SEQ ID NO. 10 or a variant oligonucleotide thereof;

(e) a set of primers comprising an oligonucleotide having a sequence given herein as SEQ ID NO. 11 or a variant oligonucleotide thereof and an oligonucleotide having a sequence given herein as SEQ ID NO. 12 or a variant oligonucleotide thereof;

(f) a set of primers comprising an oligonucleotide having a sequence given herein as SEQ ID NO. 13 or a variant oligonucleotide thereof and an oligonucleotide having a sequence given herein as SEQ ID NO. 14 or a variant oligonucleotide thereof;

(g) a set of primers comprising an oligonucleotide having a sequence given herein as SEQ ID NO. 15 or a variant oligonucleotide thereof and an oligonucleotide having a sequence given herein as SEQ ID NO. 16 or a variant oligonucleotide thereof;

(h) a set of primers comprising an oligonucleotide having a sequence given herein as SEQ ID NO. 17 or a variant oligonucleotide thereof and an oligonucleotide having a sequence given herein as SEQ ID NO. 18 or a variant oligonucleotide thereof;

(i) a set of primers comprising an oligonucleotide having a sequence given herein as SEQ ID NO. 19 or a variant oligonucleotide thereof and an oligonucleotide having a sequence given herein as SEQ ID NO. 20 or a variant oligonucleotide thereof; and (j) a set of primers comprising an oligonucleotide having a sequence given herein as SEQ ID NO. 21 or a variant oligonucleotide thereof and an oligonucleotide having a sequence given herein as SEQ ID NO. 22 or a variant oligonucleotide thereof, wherein said variant oligonucleotide is an oligonucleotide having 1 to 3 additional nucleotides joined or deleted from the 3' end, the 5' end, or both the 3' end and the 5' end of the corresponding oligonucleotide.

Another embodiment of the present invention provides a method for sequencing a human HNF-1α gene by using the primer pool.

Other embodiments of the present invention provide kits for amplifying a target sequence of a human HNF-1α gene comprising the primer pool according to the present invention.

The present invention also provides a method for amplifying a target sequence of a human HNF-1α gene comprising subjecting a target sequence of a human HNF-1α gene to a PCR which uses the primer pool according to the present invention.

BRIEF DESCRIPTION OF THE DRAWINGS

FIG. 4 illustrates a comparison of the nucleotide sequence of a single PCR product (SEQ ID. 31) obtained using a set of primers for amplifying a promoter with a known nucleotide sequence of a human HNF-1α gene.

DETAILED DESCRIPTION OF THE PREFERRED EMBODIMENTS

Figure 1:
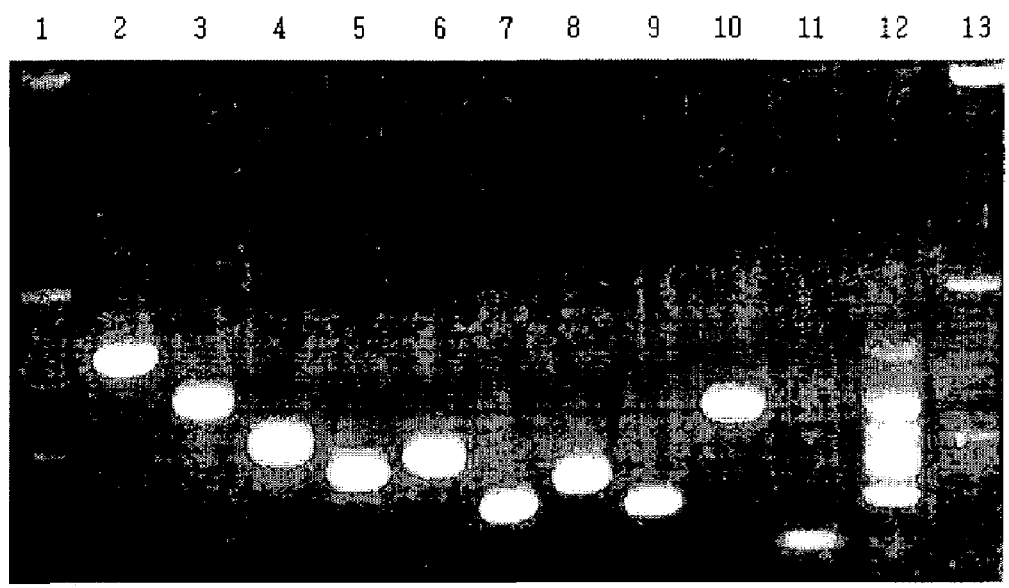
FIG. 1 illustrates an electrophoresis result of a single PCR product and a multiplex PCR product of exons 1 to 10 of a human HNF-1α gene.

To facilitate understanding of the invention, a number of terms are defined below. A "nucleic acid," as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides.

A "polynucleotide," as used herein, is a nucleic acid containing a sequence that is greater than about 100 nucleotides in length.

An "oligonucleotide," as used herein, is a short polynucleotide or a portion of a polynucleotide. An oligonucleotide typically contains a sequence of about two to about one hundred nucleotides. The word "oligo" is sometimes used in place of the word "oligonucleotide".

A base "position" as used herein refers to the location of a given base or nucleotide residue within a nucleic acid.

A "nucleic acid of interest," as used herein, is any particular nucleic acid one desires to study in a sample.

The term "isolated", when used in relation to a nucleic acid or protein, refers to a nucleic acid sequence or protein that is identified and separated from at least one contaminant (nucleic acid or protein, respectively) with which it is ordinarily associated in its natural source. As isolated nucleic acid is different from that which it is found in nature. In contrast, non-isolated nucleic acids or proteins are found in the state in which they exist in nature.

As used herein, the term "purified" or "to purify" means the result of any process which removes some contaminants from the component of interest, such as a protein or nucleic acid. The percent of a purified component is thereby increased in the sample.

The term "wild-type," as used herein, refers to a gene or gene product that has the characteristics of that gene or gene product that is most frequently observed in a population and is, thus, arbitrarily designated the "normal" or "wild-type" form of the gene. In contrast, the term "modified" or "mutant", as used herein, refers to a gene or gene product that displays modifications in sequence and/or functional properties (i.e., altered characteristics) when compared to the wild-type gene or gene product.

Nucleic acids are known to contain different types of mutations. As used herein, a "point" mutation refers to an alteration in the sequence of a nucleotide at a single base position. A "lesion", as used herein, refers to a site within a nucleic acid where one or more bases are mutated by deletion or insertion, so that the nucleic acid sequence differs from the wild-type sequence. "Insertions" or "deletions" are typically in the range of about 1 to 5 nucleic acids. The variation allowed may be experimentally determined by systematically making insertions, deletions, or substitutions of nucleic acids in a molecule using recombinant DNA techniques and assaying the resulting recombinant variants for activity.

A "single nucleotide polymorphism" or SNP, as used herein, is a variation from the most frequently occurring base at a particular nucleic acid position.

Homologous genes or alleles from different species are also known to vary in sequence. Regions of homologous genes or alleles from different species can be essentially identical in sequence. Such regions are referred to herein as "regions of identity." It is contemplated herein that a "region of substantial identity" can contain some "mismatches," where bases at the same position in the region of identity are different. This base position is referred to herein as "mismatch position." DNA molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a nucleic acid sequence, even if internal to a larger oligonucleotide or polynucleotide, also can be said to have 5'- and 3'- ends. For example, a gene sequence located within a larger chromosome sequence can still be said to have a 5'- and 3'-end.

As used herein, the 3'-terminal region of the nucleic acid probe refers to the region of the probe including nucleotides within about 10 residues from the 3'-terminal position.

In either a linear or circular DNA molecule, discrete elements are referred to as being "upstream" or "5'" relative to an element if they are bonded or would be bonded to the 5'-end of that element. Similarly, discrete elements are "downstream" or "3'" relative to an element if they are or would be bonded to the 3'-end of that element. Transcription proceeds in a 5' to 3' manner along the DNA strand. This means that RNA is made by the sequential addition of ribonucleotide-5'-triphosphates to the 3'-terminus of the growing chain (with the elimination of pyrophosphate).

As used herein, the term "target nucleic acid" or "nucleic acid target" refers to a particular nucleic acid sequence of interest. Thus, the "target" can exist in the presence of other nucleic acid molecules or within a larger nucleic acid molecule.

As used herein, the term "nucleic acid probe" refers to an oligonucleotide or polynucleotide that is capable of hybridizing to another nucleic acid of interest. A nucleic acid probe may occur naturally as in a purified restriction digest or be produced synthetically, recombinantly or by PCR amplification. As used herein, the term "nucleic acid probe" refers to the oligonucleotide or polynucleotide used in a method of the present invention. That same oligonucleotide may also be used, for example, in a PCR method as a primer for polymerization, but as used herein, that oligonucleotide would then be referred to as a "primer". Herein, oligonucleotides or polynucleotides may contain some modified linkages such as a phosphorothioate bond.

As used herein, the term "complementary" and derivatives therof are used in reference to nucleic acids (i.e., a sequence of nucleotides) related by the well-known base-pairing rules that A pairs with T and C pairs with G. For example, the sequence 5'-A-G-T-3', is complementary to the sequence 3'-T-C-A-5'. Complementarity can be "partial," in which only some of the nucleic acid bases are matched according to the base pairing rules. On the other hand, there may be "complete" or "total" complementarity between the nucleic acid strands when all of the bases are matched according to base pairing rules. The degree of complementarity between nucleic acid strands may have significant effects on the efficiency and strength of hybridization between nucleic acid strands as known well in the art. This may be of particular importance in detection methods that depend upon binding between nucleic acids, such as those of the invention. The term "substantially complementary" refers to any probe that can hybridize to either or both strands of the target nucleic acid sequence under conditions of low stringency as described below or, preferably, in polymerase reaction buffer (Promega, M195A) heated to 95° C. and then cooled to room temperature. As used herein, when the nucleic acid probe is referred to as partially or totally complementary to the target nucleic acid, that refers to the 3'-terminal region of the probe (i.e. within about 10 nucleotides of the 3'-terminal nucleotide position).

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence. Hybridization of such sequences as disclosed in the present invention may be carried out under conditions of reduced stringency or even stringent conditions (e.g., conditions represented by a wash stringency of 0.3 M NaCl, 0.03 M sodium citrate, 0.1% SDS at 60° C. or even 70° C. to DNA herein in a standard in situ hybridization assay. See J. Sambrook et al., Molecular Cloning, A Laboratory Manual (2d Ed. 1989)(Cold Spring Harbor Laboratory)). In general, such sequences will be at least 65% similar, 75% similar, 80% similar, 85% similar, 90% similar, or even 95% similar, or more, with the sequences given herein.

A multiplex method of this invention may be used to determine the presence or absence of a plurality of predetermined (known) nucleic acid target sequences in a nucleic acid sample. A nucleic acid target is "predetermined" in that its sequence must be known to design a probe that hybridizes with that target. However, it should be noted that a nucleic acid target sequence, as used with respect to a process of this invention, may be able to act as a reporter to signal the presence of a different nucleic acid whose presence is desired to be determined. The other nucleic acid of interest does not necessarily have to have a predetermined sequence. Furthermore, the invention may be useful in determining the identity of a base within a target in which only enough of the sequence is known to design a probe that hybridizes to that target with partial complementarity at the 3'-terminal region of the probe. Such a method utilizes an enzyme that can depolymerize the 3'-terminus of an oligonucleotide probe hybridized to the nucleic acid target sequence to release one or more identifier nucleotides whose presence or absence can then be determined as an analytical output that indicates the presence or absence of the target sequence.

A nucleic acid target sequence may be predetermined in that a nucleic acid probe is provided to be partially or totally complementary to that nucleic acid target sequence. Such nucleic acid target sequence is a portion of nucleic acid sample with which the probe hybridizes if that target sequence is present in the sample.

The present invention includes methods of admixing a sample to be assayed with a plurality of nucleic acid probes. The admixing of the first step is typically carried out under low stringency hybridizing conditions to form a hybridization composition. In such a hybridization composition, the 3'-terminal region of the nucleic acid probes (i) hybridize with partial or total complementarity to a nucleic acid target sequence that may be present in the sample; and (ii) include an identifier nucleotide in the 3'-terminal region.

The nucleic acid probe may be designed so as not hybridize with itself to form a hairpin structure in such a way as to interfere with hybridization of the 3'-terminal region of the probe to the target nucleic acid. Parameters guiding probe design are well known in the art.

The hybridization composition may be maintained under hybridizing conditions for a time period sufficient to form a treated sample that may contain a plurality of predetermined nucleic acid target sequences hybridized with their respective nucleic acid probes.

In the event that the sample to be assayed does not contain a target sequence to which a probe hybridizes, no hybridization takes place for that probe. When a method of the present invention is used to determine whether a particular target sequence is present or absent in a sample to be assayed, the resulting treated sample may not contain a substrate for the enzymes of the present invention. As a result, a 3' terminal region identifier nucleotide is not released and the analytical output is at or near background levels.

In developing a primer pool for amplifying a human HNF-1α gene by a multiplex PCR, the following factors may be taken into consideration:

A primer of the primer pool should be able to bind to a target sequence of a human HNF-1α gene and should not interfere with each other in order to amplify a target sequence in a sufficient amount. Each primer of a primer pool will likely have a similar melting temperature and preferably should not form a primer pair-dimer. In addition, each primer of a primer pool should not form a hairpin or primer self-dimer. A microsatellite region and a repetitive region may be excluded from a primer sequence.

A primer pool for amplifying target sequences of a human HNF-1α gene includes at least one set of primers for amplifying target sequences of a human HNF-1α gene selected from the group consisting of:

(a) a set of primers comprising an oligonucleotide having a sequence given herein as SEQ ID NO. 3 or a variant oligonucleotide thereof and an oligonucleotide having a sequence given herein as SEQ ID NO. 4 or a variant oligonucleotide thereof;

(b) a set of primers comprising an oligonucleotide having a sequence given herein as SEQ ID NO. 5 or a variant oligonucleotide thereof and an oligonucleotide having a sequence given herein as SEQ ID NO. 6 or a variant oligonucleotide thereof;

(c) a set of primers comprising an oligonucleotide having a sequence given herein as SEQ ID NO. 7 or a variant oligonucleotide thereof and an oligonucleotide having a sequence given herein as SEQ ID NO. 8 or a variant oligonucleotide thereof;

(d) a set of primers comprising an oligonucleotide having a sequence given herein as SEQ ID NO. 9 or a variant oligonucleotide thereof and an oligonucleotide having a sequence given herein as SEQ ID NO. 10 or a variant oligonucleotide thereof;

(e) a set of primers comprising an oligonucleotide having a sequence given herein as SEQ ID NO. 11 or a variant oligonucleotide thereof and an oligonucleotide having a sequence given herein as SEQ ID NO. 12 or a variant oligonucleotide thereof;

(f) a set of primers comprising an oligonucleotide having a sequence given herein as SEQ ID NO. 13 or a variant oligonucleotide thereof and an oligonucleotide having a sequence given herein as SEQ ID NO. 14 or a variant oligonucleotide thereof;

(g) a set of primers comprising an oligonucleotide having a sequence given herein as SEQ ID NO. 15 or a variant oligonucleotide thereof and an oligonucleotide having a sequence given herein as SEQ ID NO. 16 or a variant oligonucleotide thereof;

(h) a set of primers comprising an oligonucleotide having a sequence given herein as SEQ ID NO. 17 or a variant oligonucleotide thereof and an oligonucleotide having a sequence given herein as SEQ ID NO. 18 or a variant oligonucleotide thereof;

(i) a set of primers comprising an oligonucleotide having a sequence given herein as SEQ ID NO. 19 or a variant oligonucleotide thereof and an oligonucleotide having a sequence given herein as SEQ ID NO. 20 or a variant oligonucleotide thereof; and (j) a set of primers comprising an oligonucleotide having a sequence given herein as SEQ ID NO. 21 or a variant oligonucleotide thereof and an oligonucleotide having a sequence given herein as SEQ ID NO. 22 or a variant oligonucleotide thereof, wherein said variant oligonucleotide is an oligonucleotide having 1 to 3 additional nucleotides joined or deleted from the 3' end, the 5' end, or both the 3' end and the 5' end of the corresponding oligonucleotide.

Thus, the variant oligonucleotide has the same nucleotide sequence as that of the corresponding oligonucleotide except for at least one terminus portion thereof.

The present invention also includes kits for amplifying a target sequence of a human HNF-1α gene according to the present invention comprises a primer pool. The kit may comprise of a conventional reagent for PCR such as a dNTP solution, DNA polymerase and buffers and the like Additionally, the present invention may be used in determining the genetic variation of a human HNF-1α gene. One such variation includes MODY 3, a kind of MODY disease (MODY 1, 2, 3, 4 and 5), which accounts for about 10–30% of all type II diabetes mellitus cases. Thus, in analyzing a genetic variation of a human HNF-1α gene, it is possible to anticipate a person's propensity to a diabetes mellitus. Therefore, in order to rapidly analyze a human HNF-1α gene using, for example, a DNA chip, a set of primers for amplifying a human HNF-1α gene by a multiplex PCR may be developed.

The present invention will be described in further detail with reference to the following examples. The following examples are for illustrative purposes and are not intended to limit the scope of the invention.

EXAMPLE 1

Preparation of Primers for Amplifying 10 Target Sequences of a Human HNF-1α Gene Primers were designed so that the size of each PCR product differs by at least 5–10 bp. In designing a set of primers for a multiplex PCR, the above described factors were taken into consideration. Furthermore, each primer was designed so as not to include four or more identical consecutive nucleotides.

HYBsimulator™ (Advanced Gene Computing Technologies, Inc) was used to analyze the primer.

To improve an amplification efficiency of a PCR product, a T7 promoter sequence (SEQ ID NO. 1) was added at 5' end of a forward primer and a T3 promoter sequence (SEQ ID NO. 2) was added at 5' end of a reverse primer.

The sequence number and characteristics for each primer are listed in Table 1.

TABLE 1

|     | Primers    | sequence      | size | Tm (° C.) | PCR product (bp) |
|-----|------------|---------------|------|-----------|------------------|
| Set | Promoter-F | SEQ ID NO. 3  | 21   | 74.1      | 540              |
|     | Promoter-R | SEQ ID NO. 4  | 21   | 73.6      |                  |
| Set | Exon1-F    | SEQ ID NO. 5  | 20   | 77.5      | 420              |
|     | Exon1-R    | SEQ ID NO. 6  | 21   | 72.3      |                  |
| Set | Exon2-F    | SEQ ID NO. 7  | 22   | 72.7      | 326              |
|     | Exon2-R    | SEQ ID NO. 8  | 21   | 71        |                  |
| Set | Exon3-F    | SEQ ID NO. 9  | 20   | 71.1      | 269              |
|     | Exon3-R    | SEQ ID NO. 10 | 23   | 69.6      |                  |
| Set | Exon4-F    | SEQ ID NO. 11 | 23   | 70        | 293              |
|     | Exon4-R    | SEQ ID NO. 12 | 23   | 76.3      |                  |
| Set | Exon5-F    | SEQ ID NO. 13 | 22   | 73.6      | 202              |
|     | Exon5-R    | SEQ ID NO. 14 | 23   | 70        |                  |
| Set | Exon6-F    | SEQ ID NO. 15 | 21   | 71.25     | 247              |
|     | Exon6-R    | SEQ ID NO. 16 | 23   | 72        |                  |
| Set | Exon7-F    | SEQ ID NO. 17 | 20   | 75.99     | 191              |
|     | Exon7-R    | SEQ ID NO. 18 | 21   | 74.17     |                  |
| Set | Exon8&9-F  | SEQ ID NO. 19 | 21   | 76.16     | 375              |
|     | Exon8&9-R  | SEQ ID NO. 20 | 21   | 73.14     |                  |
| Set | Exon10-F   | SEQ ID NO. 21 | 21   | 68.05     | 132              |
|     | Exon10-R   | SEQ ID NO. 22 | 22   | 70.53     |                  |

F: forward
R: reverse

EXAMPLE 2

Amplification of a Human HNF-1α Gene by a Single PCR

Each target sequence of a human HNF-1α gene was amplified by a single PCR using each set of primers according to Example 1. The PCR was completed through initial denaturation (5 mins at 95° C.), 30 cycles of denaturation (30 secs at 95° C.), annealing (15 secs at 64° C.) and polymerization (30 secs at 72° C.), and final extension (3 mins at 72° C.). The composition of a reaction solution for the PCR was as follows:

| Sterilized DNase and RNase free water | 12.8 μl |
|---|---|
| dNTP mix (each nucleotide 2.5 mM) | 2 μl |
| 10× Taq polymerase buffer | 2 μl |
| a set of primers (each primer 10 pmol) | 2 μl |
| genomic DNA (200–1.0 μg) | 1 μl |
| Taq polymerase (5 unit/μl) | 0.2 μl |

The PCR product was analyzed by electrophoresis with 1.8% agarose gel (FIG. 1). In FIG. 1, lanes 1 and 13 represent molecular markers, 50 bp DNA ladders. Lane 2 represents a PCR products corresponding to promoter, and lanes 3–11 represent PCR products corresponding exons 1, 2, 3, 4, 5, 6, 7, 8 & 9 and 10, respectively. Lane 12 represents a multiplex PCR product according to the following Example 3.

As shown in FIG. 1, a target sequence of a human HNF-1α gene was amplified by a single PCR using a set of primers according to Example 1.

EXAMPLE 3

Amplification of a Human HNF-1α Gene by a Multiplex PCR

A multiple PCR was conducted by using a set of primers according to Example 1. The reaction was conducted through initial denaturation (5 mins at 95° C.), 30 cycles of denaturation (30 secs at 95° C.), annealing (15 secs at 64° C.) and polymerization (30 secs at 72° C.), and final extension (3 mins at 72° C.). All the primers were added in a single reaction tube. The composition of the reaction solution was as follows:

| Sterilized DNase and RNase free water | 18.4 μl |
|---|---|
| dNTP mix (each nucleotide 2.5 mM) | 5 μl |
| 10× Taq polymerase buffer | 5 μl |
| a set of primers (each primer 10 pmol) | 20 μl |
| genomic DNA (200–1.0 μg) | 1 μl |
| Taq polymerase (5 unit/μl) | 0.6 μl |

The PCR product was analyzed by an electrophoresis with 1.8% agarose gel (FIG. 1 lane 12). As shown in FIG. 1, as a result of a multiplex PCR using the set of primers according to Example 1, all of the 10 target sequences (579, 459, 365, 308, 332, 241, 286, 230, 414, and 171 bp) of a human HNF-1α gene were amplified.

EXAMPLE 4

Figure 2:
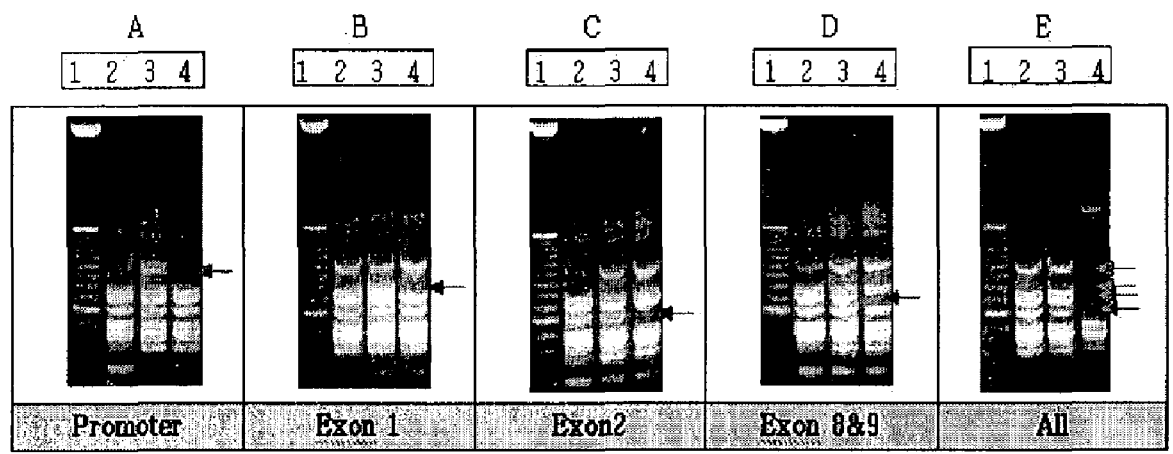
FIGS. 2A through 2E depict an electrophoresis result of a multiplex PCR product obtained using a set of variant primers.

Amplification of a Human HNF-1α Gene by a Multiplex PCR Using a Set of Variant Primers A set of variant primers was synthesized by adding 3 nucleotides complementary to the template at one end of 4 sets of primers (primers sets for amplifying promoter, exons 1, 2 and 8) and by deleting 3 nucleotides at the other end of each primer (Table 2). A multiplex PCR was conducted by the same method as described in the Example 3 except that one set of primers among above 4 sets of primers and the other 3 corresponding sets of primers shown in Table 1 were used (FIG. 2).

TABLE 2

| Primers | Sequences | |
|---|---|---|
| Promoter-F | t̶g̶g̶ccgtgagcatcctctgccctt | (SEQ ID NO.23) |
| Promoter-R | accgcgtgggttgcgtttgcct̶g̶g̶ | (SEQ ID NO.24) |
| Exon 1-F | ccgcgtggccctgtggcagt̶g̶a̶ | (SEQ ID NO.25) |
| Exon1-R | gggctcgttaggagctgaggggg | (SEQ ID NO.26) |
| Exon2-F | c̶c̶c̶ttgctgagcagatcccgtcctt | (SEQ ID NO.27) |
| Exon2-R | atggggatggtgaagcttccag̶c̶c̶ | (SEQ ID NO.28) |
| Exon8-F | ggtggcccagtacacccacag̶g̶g̶ | (SEQ ID NO.29) |
| Exon8-R | g̶g̶g̶cagggacagtaagggaggggg | (SEQ ID NO.30) |

F: forward
R: reverse
x̶x̶x̶: deleted nucleotides from the corresponding primer shown in Table 1.
xxx: added nucleotides to the corresponding primer shown in Table 1.

FIGS. 2A through 2E are photographs for illustrating electrophoresis results of a obtained using a primer pool comprising a set of variant primers for amplifying promoter, exon 1, 2 or 8 shown in Table 2. FIG. 2E illustrates an electrophoresis result of a multiplex PCR product obtained using a primer pool comprising all said sets of variant primers for promoter, exons 1, 2 and 8. In FIGS. 2A through 2E, the lane 1 represents a molecular marker, a 50 bp DNA ladder. Lane 2 represents a multiplex PCR result obtained by using a set of primers listed in Table 1, lane 3 represents a multiplex PCR result obtained by using a primer pool comprising a set of variant primers for promoter, exons 1, 2 or 8 listed in Table 2 and a set of primers listed in Table 1 without the corresponding set of variant primers, and lane 4 represents a multiplex PCR result obtained by using a primer pool comprising a set of primers listed in Table 1 without the set of primers for amplifying promoter, exon 1, 2 or 8 (FIGS. 2A, B, C and D) or without the set of primers for amplifying promoter, exon 1, 2 and 8 (FIG. 2E).

As shown in FIG. 2, a corresponding target sequence of a gene was amplified by a multiplex PCR using a set of variant primers.

EXAMPLE 5

Identification of a Multiplex PCR Product Through a Southern Blotting Analysis

PCR products amplified according to Examples 2 and 3 were electrophoresed with 1.8% agarose gel (FIG. 1). The gel was added into a denaturation solution (0.5N NaOH+ 1.5M NaCl) with stirring for 15 minutes to denature the double-stranded DNA. After performing the denaturation process twice, repeating two times, the gel was washed with distilled water, then the gel was added into a neutralization solution (3M NaCl containing 0.5M Tris-HCl, pH 7.5) for 15 minutes with gentle stirring to neutralize the gel. After performing the neutralization procedure twice, a DNA within the gel was transferred to a nylon membrane by reacting the gel with the nylon membrane in 20×SSC solution for 12.5 hours. The DNA was cross-linked to the nylon membrane by reacting for 30 minutes at 120° C., and the membrane was washed for 1–2 minutes and dried.

The obtained DNA attached-membrane was then put into 20 ml of a hybridization solution for about 2 hours at 62° C. for prehybridization and the solution was discarded. The DNA attached-membrane and 5 pmol/ml of DIG (digoxigenin) labeled probe were added into 10 ml of a fresh hybridization solution bag and reacted for about 12 hours at 62° C. During the reaction, the DIG labeled probe hybridized to a complementary region of a gene. After the reaction, the membrane was washed twice with 2× washing solution (2×SSC+0.1% SDS) for 5 minutes at room temperature, and washed twice with 0.5× washing solution (0.5×SSC+0.1% SDS) for 15 minutes at 62° C.

Figure 3:
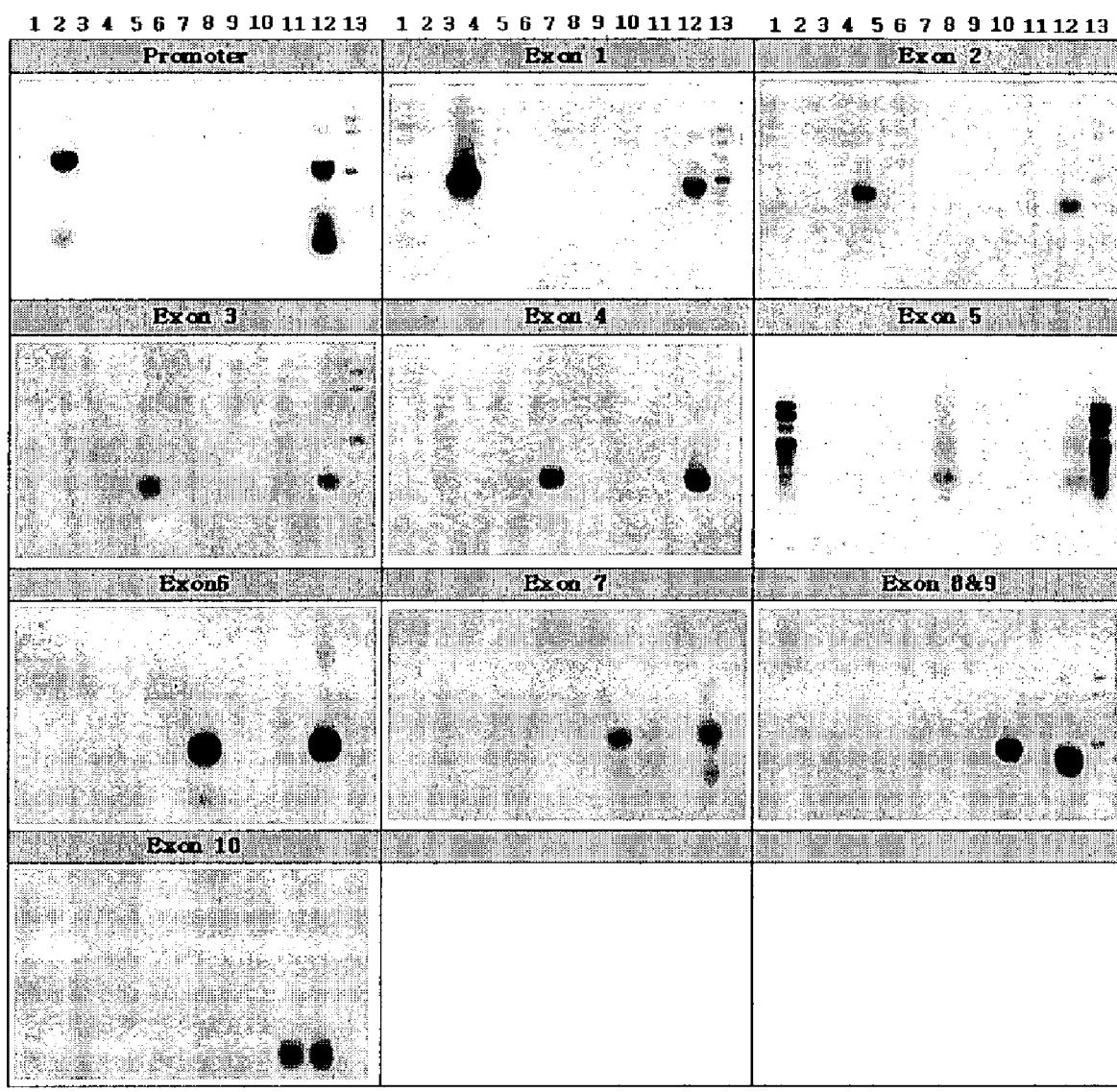
FIG. 3 is a photograph for illustrating a Southern blotting result of a single PCR and a multiplex PCR obtained using each primer set for amplifying each exon as a probe.

The membrane was introduced into 20 ml of a blocking solution for about 30–60 minutes, then the membrane was reacted with anti-DIG antibody in 20 ml of the blocking solution containing 1 μl of an alkaline phosphatase-conjugated sheep anti-DIG antibody (Roche) for about 30 minutes. The membrane was then washed twice with a washing solution (100 mM maleic acid, 150 mM NaCl, pH 7.5 at room temperature, 0.3% Tween 20) for about 15 minutes. To confirm the hybridization between DNA and a probe on the membrane, an alkaline phosphatase substrate, CDP-Star was mixed with a detection buffer solution with a ratio of 1:100 and the membrane was treated with this solution for about 5 minutes, and an X-ray film was exposed to this membrane. The film was developed to confirm the position of a probe (FIG. 3). As shown in FIG. 3, lane 13 represents a molecular marker labeled with DIG, and each of 2 through 11 represents a single In FIG. 3, lane 13 represents a molecular marker labeled with DIG, and each of lanes 2 through 11 represents a single PCR product of promoter, or exons 1, 2, 3, 4, 5, 6, 7, 8 & 9, or 10 respectively. Lane 12 represents a multiplex, PCR product.

As shown in FIG. 3, the probe hybridized into a single PCR product and a multiplex PCR product at the same position, which means that the amplified product is substantially identical.

EXAMPLE 6

Identification of a Multiplex PCR Product Through a Sequencing Analysis

A multiplex PCR product amplified according to Examples 3 was electrophoresed with 1.8% agarose gel. An Individual DNA band was isolated, and purified with a gel extraction kit. The sequence of the purified DNA was identified by ABl3700, and compared with a corresponding known sequence of a human HNF-1α gene (FIG. 4).

FIG. 4 illustrates a PCR product corresponding to a PCR product obtained by using a set of primers for amplifying promoter. The PCR product corresponding to a PCR product obtained by using a set of primers SEQ ID NOS. 3 and 4 in a multiplex PCR was isolated and sequenced by using an automatic sequencing method. The resultant nucleotide sequence (SEQ ID NO. 31) (referred to as "Query") was compared with a known sequence of a human HNF-1α gene promoter (referred to as "Promoter") by a program called Lagergene (DNAstar Inc.) (FIG. 4). As shown in FIG. 4, the PCR product showed 100% sequence homology with the known sequence of a human HNF-1α promoter. The gap frequency used in the alignment was 0%. In addition to the promoter, single PCR products of the other exons were also sequenced and analyzed in the same way as described above, and each PCR product showed 95% or more of homologies with a known corresponding exon sequence.

EXAMPLE 7

Stability Test of a Reaction Solution for the Multiplex PCR

Figure 5:
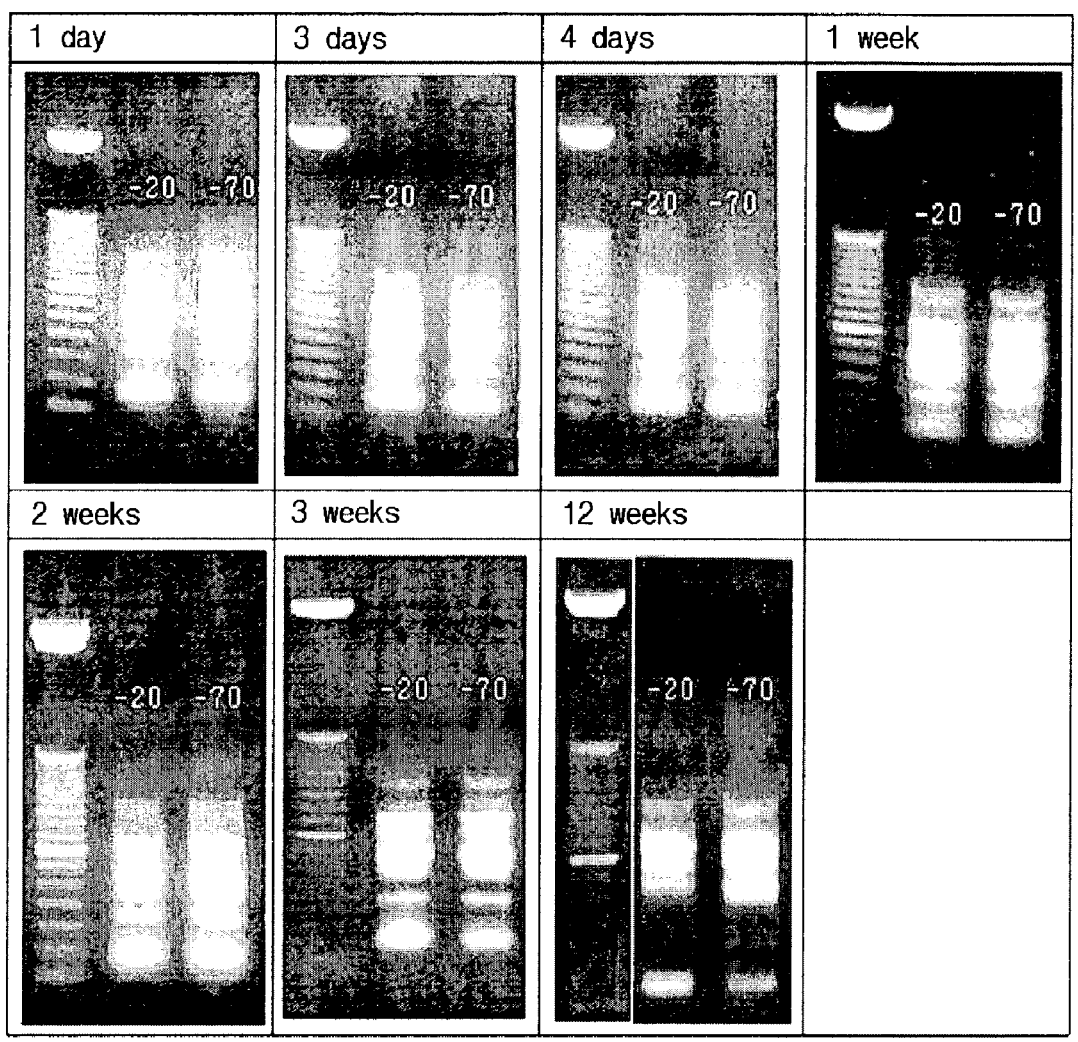
FIG. 5 illustrates the result of a stability test of a reaction solution for a multiplex PCR.

The reaction solution for the multiplex PCR used in Example 3 was prepared in large quantities, excluding genomic DNA, to test the stability thereof. An amount of 49 μl of the reaction solution, which was required for one PCR, was alliquoted into each of a plurality of 0.2 ml-PCR tubes. Some of the tubes including the reaction solution were kept at −20° C., and others were kept at −70° C., for three months. Multiplex PCR was performed using the reaction solution in the tube at 1 day, 3 days, 4 days, 1 week, 2 weeks, 3 weeks, and 12 weeks, respectively. FIG. 5 shows the electrophoresis results of the multiplex PCR products. In FIG. 5, the first lane from the left is a molecular marker, lane 2 is a multiplex PCR result obtained using a reaction solution kept at −20° C., and lane 3 is a multiplex PCR result obtained using a reaction solution kept at −70° C. As shown in FIG. 5, the reaction solution for the multiplex PCR used in the present invention was stable at −20° C. or −70° C., and it did not degenerate PCR product therein even after a period of three months.

EXAMPLE 8

Gene Amplifications when Using Various PCR Devices

Multiplex PCRs were conducted according to the method of Example 3 using various PCR devices. The amplified multiplex PCR products were electrophoresed with 1.8% agarose gel to examine the dependency of the PCR products upon PCR device (FIGS. 6A through C).

FIG. 6A represents the multiplex PCR product amplified using PTC-100 (MJ Research Co.), FIG. 6B represents the multiplex PCR product amplified using GeneAmp 9700 (Applied Biosystems Co.), and FIG. 6C represents the multiplex PCR product amplified using Multi-Block System (ThermoHybaid Co.).

In FIGS. 6A to 6C, the lane 1 is a molecular marker, a 50 bp DNA ladder, and lane 2 is a multiplex PCR result obtained by using a set of primers shown in Table 1. Arrows in the figure represent 350 bp and 50 bp, respectively.

Figure 6:
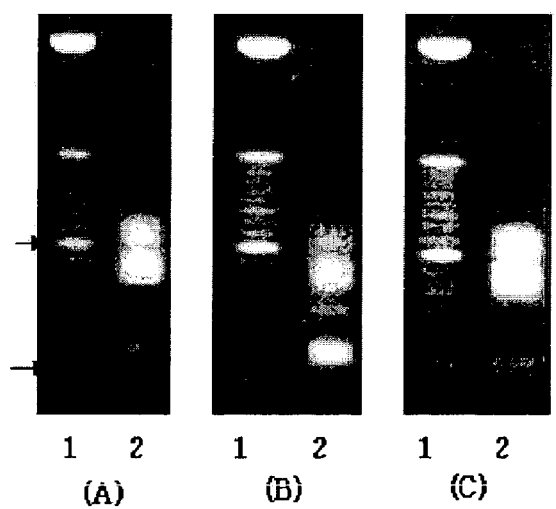
FIG. 6 is a photograph for illustrating electrophoresis results of multiplex PCR products obtained using three different amplification devices.

As shown in FIG. 6, similar PCR product-patterns were obtained independently of PCR devices, which indicates that the PCR product obtained by using a set of primers of the present invention is stable and economical.

The primer pool for amplifying a human HNF-1α gene of the present invention is effective in amplifying a corresponding gene by a multiplex PCR. Particularly, the primer pool for amplifying a gene by a multiplex PCR is useful for an analysis of a disease-associated gene by using a DNA chip since the multiplex PCR requires relatively a reduced number of samples.

The primer pool for amplifying a human HNF-1α gene of the present invention may then be applied to a kit for amplifying or sequencing a human HNF-1α gene.

In the specification, there have been disclosed typical preferred embodiments of the invention and, although specific terms are employed, they are used in a generic and descriptive sense only and not for purposes of limitation of the scope of the invention, that being set forth in the following claims.

What is claimed is:

1. A primer pool for amplifying 10 target sequences of a human HNF-1α gene, wherein each of the primer set (a) to (j) amplifies a particular target sequence, comprising:
   (a) a set of primers comprising an oligonucleotide consisting of SEQ ID NO. 3 and an oligonucleotide consisting of SEQ ID NO. 4;
   (b) a set of primers comprising an oligonucleotide consisting of SEQ ID NO. 5 and an oligonucleotide consisting of SEQ ID NO. 6;
   (c) a set of primers comprising an oligonucleotide consisting of SEQ ID NO. 7 and an oligonucleotide consisting of SEQ ID NO. 8;
   (d) a set of primers comprising an oligonucleotide consisting of SEQ ID NO. 9 and an oligonucleotide consisting of SEQ ID NO. 10;
   (e) a set of primers comprising an oligonucleotide consisting of SEQ ID NO. 11 and an oligonucleotide consisting of SEQ ID NO. 12;
   (f) a set of primers comprising an oligonucleotide consisting of SEQ ID NO. 13 and an oligonucleotide consisting of SEQ ID NO. 14;
   (g) a set of primers comprising an oligonucleotide consisting of SEQ ID NO. 15 and an oligonucleotide consisting of SEQ ID NO. 16;
   (h) a set of primers comprising an oligonucleotide consisting of SEQ ID NO. 17 and an oligonucleotide consisting of SEQ ID NO. 18;
   (i) a set of primers comprising an oligonucleotide consisting of SEQ ID NO. 19 and an oligonucleotide consisting of SEQ ID NO. 20; and
   (j) a set of primers comprising an oligonucleotide consisting of SEQ ID NO. 21 and an oligonucleotide consisting of SEQ ID NO. 22.

2. The primer pool of claim 1, wherein at least one of the primers includes a T7 promoter sequence or a T3 promoter sequence at its 5' terminal.

3. The primer pool of claim 1, wherein at least one of the primers consisting of the SEQ ID NOS. 3, 5, 7, 9, 11, 13, 15, 17, 19 and 21 includes a T7 promoter sequence at its 5' terminal and at least one of the primers consisting of the SEQ ID NOS. 4, 6, 8, 10, 12, 14, 16, 18, 20 and 22 includes a T3 promoter sequence at its 5' terminal.

4. A method for amplifying 10 target sequences of a human HNF-1α gene, wherein each of the primer set (a) to (j) amplifies a particular target sequence, comprising:
   subjecting the 10 target sequences of a human HNF-1α gene to a PCR using a primer pool comprising:
   (a) a set of primers comprising an oligonucleotide consisting of SEQ ID NO. 3 and an oligonucleotide consisting of SEQ ID NO. 4;
   (b) a set of primers comprising an oligonucleotide consisting of SEQ ID NO. 5 and an oligonucleotide consisting of SEQ ID NO. 6;

(c) a set of primers comprising an oligonucleotide consisting of SEQ ID NO. 7 and an oligonucleotide consisting of SEQ ID NO. 8;

(d) a set of primers comprising an oligonucleotide consisting of SEQ ID NO. 9 and an oligonucleotide consisting of SEQ ID NO. 10;

(e) a set of primers comprising an oligonucleotide consisting of SEQ ID NO. 11 and an oligonucleotide consisting of SEQ ID NO. 12;

(f) a set of primers comprising an oligonucleotide consisting of SEQ ID NO. 13 and an oligonucleotide consisting of SEQ ID NO. 14;

(g) a set of primers comprising an oligonucleotide consisting of SEQ ID NO. 15 and an oligonucleotide consisting of SEQ ID NO. 16;

(h) a set of primers comprising an oligonucleotide consisting of SEQ ID NO. 17 and an oligonucleotide consisting of SEQ ID NO. 18thereof;

(i) a set of primers comprising an oligonucleotide consisting of SEQ ID NO. 19 and an oligonucleotide consisting of SEQ ID NO. 20; and (j) a set of primers comprising an oligonucleotide consisting of SEQ ID NO. 21 and an oligonucleotide consisting of SEQ ID NO. 22.

5. The method according to claim 4, wherein at least one of the primers includes a T7 promoter sequence or a T3 promoter sequence at its 5' terminal.

6. The method according to claim 4, wherein at least one of the primers consisting of the SEQ ID NOS. 3, 5, 7, 9, 11, 13, 15, 17, 19 and 21 includes a T7 promoter sequence at its 5' terminal and at least one of the primers consisting of the SEQ ID NOS. 4, 6, 8, 10, 12, 14, 16, 18, 20 and 22 includes a T3 promoter sequence at its 5' terminal.

7. The method of claim 4, further comprising mixing 0.1 μM–1 μM of each of the primers with 100 ng–1 μg of a template DNA.

8. The method of claim 4, wherein the PCR is conducted in the conditions of initial denaturation for 1–5 min at 90° C.–98° C., denaturation for 10 sec to 1 min at 90° C.–98° C., annealing for 5 sec–3 min at 60° C.–65° C., polymerization for 5 sec–5 min at 70° C.–75° C. and final extension for 1 min to 10 min at 70° C.–75° C.

9. A method for sequencing 10 target nucleotide sequences of a human HNF-1α gene, wherein each of the primer set (a) to (j) amplifies a particular target sequence, comprising:

sequencing the 10 target nucleotide sequences of the human HNF-1α by using a primer pool comprising:

(a) a set of primers comprising an oligonucleotide consisting of SEQ ID NO. 3 and an oligonucleotide consisting of SEQ ID NO. 4;

(b) a set of primers comprising an oligonucleotide consisting of SEQ ID NO. 5 and an oligonucleotide consisting of SEQ ID NO. 6;

(c) a set of primers comprising an oligonucleotide consisting of SEQ ID NO. 7 and an oligonucleotide consisting of SEQ ID NO. 8;

(d) a set of primers comprising an oligonucleotide consisting of SEQ ID NO. 9 and an oligonucleotide consisting of SEQ ID NO. 10;

(e) a set of primers comprising an oligonucleotide consisting of SEQ ID NO. 11 and an oligonucleotide consisting of SEQ ID NO. 12;

(f) a set of primers comprising an oligonucleotide consisting of SEQ ID NO. 13 and an oligonucleotide consisting of SEQ ID NO. 14;

(g) a set of primers comprising an oligonucleotide consisting of SEQ ID NO. 15 and an oligonucleotide consisting of SEQ ID NO. 16;

(h) a set of primers comprising an oligonucleotide consisting of SEQ ID NO. 17 and an oligonucleotide consisting of SEQ ID NO. 18;

(i) a set of primers comprising an oligonucleotide consisting of SEQ ID NO. 19 and an oligonucleotide consisting of SEQ ID NO. 20; and (j) a set of primers comprising an oligonucleotide consisting of SEQ ID NO. 21 and an oligonucleotide consisting of SEQ ID NO. 22.

10. The method according to claim 9, wherein at least one of the primers includes a T7 promoter sequence or a T3 promoter sequence at its 5' terminal.

11. The method according to claim 9, wherein at least one of the primers consisting of the SEQ ID NOS. 3, 5, 7, 9, 11, 13, 15, 17, 19 and 21 includes a T7 promoter sequence at its 5' terminal and at least one of the primers consisting of the SEQ ID NOS. 4, 6, 8, 10, 12, 14, 16, 18, 20 and 22 includes a T3 promoter sequence at its 5' terminal.

12. A kit for amplifying 10 target sequences of a human HNF-1α gene comprising a primer pool, wherein each of the primer set (a) to (j) amplifies a particular target sequence, consisting of:

(a) a set of primers comprising an oligonucleotide consisting of SEQ ID NO. 3 and an oligonucleotide consisting of SEQ ID NO. 4;

(b) a set of primers comprising an oligonucleotide consisting of SEQ ID NO. 5 and an oligonucleotide consisting of SEQ ID NO. 6;

(c) a set of primers comprising an oligonucleotide consisting of SEQ ID NO. 7 and an oligonucleotide consisting of SEQ ID NO. 8;

(d) a set of primers comprising an oligonucleotide consisting of SEQ ID NO. 9 and an oligonucleotide consisting of SEQ ID NO. 10;

(e) a set of primers comprising an oligonucleotide consisting of SEQ ID NO. 11 and an oligonucleotide consisting of SEQ ID NO. 12;

(f) a set of primers comprising an oligonucleotide consisting of SEQ ID NO. 13 and an oligonucleotide consisting of SEQ ID NO. 14;

(g) a set of primers comprising an oligonucleotide consisting of SEQ ID NO. 15 and an oligonucleotide consisting of SEQ ID NO. 16;

(h) a set of primers comprising an oligonucleotide consisting of SEQ ID NO. 17 and an oligonucleotide consisting of SEQ ID NO. 18;

(i) a set of primers comprising an oligonucleotide consisting of SEQ ID NO. 19 and an oligonucleotide consisting of SEQ ID NO. 20; and (j) a set of primers comprising an oligonucleotide consisting of SEQ ID NO. 21 and an oligonucleotide consisting of SEQ ID NO. 22.

13. The kit of claim 12, wherein at least one of the primers includes a T7 promoter sequence or a T3 promoter sequence at its 5' terminal.

14. The kit of claim 12, wherein at least one of the primers consisting of the SEQ ID NOS. 3, 5, 7, 9, 11, 13, 15, 17, 19 and 21 includes a T7 promoter sequence at its 5' terminal and at least one of the primers consisting of the SEQ ID NOS. 4, 6, 8, 10, 12, 14, 16, 18, 20 and 22 includes a T3 promoter sequence at its 5' terminal.

15. A method of characterizing a test sample for maturity-onset diabetes in the young, MODY 3 comprising:
amplifying 10 target sequences of a human HNF-1α gene with a primer pool, wherein each of the primer set (a) to (j) amplifies a particular target sequence, consisting of:
(a) a set of primers comprising an oligonucleotide consisting of SEQ ID NO. 3 and an oligonucleotide consisting of SEQ ID NO. 4;
(b) a set of primers comprising an oligonucleotide consisting of SEQ ID NO. 5 and an oligonucleotide consisting of SEQ ID NO. 6;
(c) a set of primers comprising an oligonucleotide consisting of SEQ ID NO. 7 and an oligonucleotide consisting of SEQ ID NO. 8;
(d) a set of primers comprising an oligonucleotide consisting of SEQ ID NO. 9 and an oligonucleotide consisting of SEQ ID NO. 10;
(e) a set of primers comprising an oligonucleotide consisting of SEQ ID NO. 11 and an oligonucleotide consisting of SEQ ID NO. 12;
(f) a set of primers comprising an oligonucleotide consisting of SEQ ID NO. 13 and an oligonucleotide consisting of SEQ ID NO. 14;
(g) a set of primers comprising an oligonucleotide consisting of SEQ ID NO. 15 and an oligonucleotide consisting of SEQ ID NO. 16;
(h) a set of primers comprising an oligonucleotide consisting of SEQ ID NO. 17 and an oligonucleotide consisting of SEQ ID NO. 18;
(i) a set of primers comprising an oligonucleotide consisting of SEQ ID NO. 19 and an oligonucleotide consisting of SEQ ID NO. 20; and
(j) a set of primers comprising an oligonucleotide consisting of SEQ ID NO. 21 and an oligonucleotide consisting of SEQ ID NO. 22, and
testing the amplified target sequences for deletions, mutations, and polymorphisms to characterize the test sample for MODY3.

16. The method according to claim 15, further comprising adding a label to the nucleic acid sequences in said sample before hybridizing them to oligonucleotides in a microchip.

17. The method according to claim 15, wherein at least one of the primers includes a T7 promoter sequence or a T3 promoter sequence at its 5' terminal.

18. The method according to claim 15, wherein at least one of primers consisting of the SEQ ID NOS. 3, 5, 7, 9, 11, 13, 15, 17, 19 and 21 includes a T7 promoter sequence at its 5' terminal and at least one of primers consisting of the SEQ ID NOS. 4, 6, 8, 10, 12, 14, 16, 18, 20 and 22 includes a T3 promoter sequence at its 5' terminal.

* * * * *

SEQUENCE LISTING

```
<160> NUMBER OF SEQ ID NOS: 31

<210> SEQ ID NO 1
<211> LENGTH: 20
<212> TYPE: DNA
<213> ORGANISM: Bacteriophage T7

<400> SEQUENCE: 1
taatacgact cactataggg                                              20

<210> SEQ ID NO 2
<211> LENGTH: 19
<212> TYPE: DNA
<213> ORGANISM: Bacterophage T3

<400> SEQUENCE: 2
gtaaccctca ctaaaggga                                               19

<210> SEQ ID NO 3
<211> LENGTH: 21
<212> TYPE: DNA
<213> ORGANISM: Artificial Sequence
<220> FEATURE:
<223> OTHER INFORMATION: forward primer for amplifying promoter of
      MODY3 gene

<400> SEQUENCE: 3
tggccgtgag catcctctgc c                                            21

<210> SEQ ID NO 4
<211> LENGTH: 21
<212> TYPE: DNA
<213> ORGANISM: Artificial Sequence
<220> FEATURE:
<223> OTHER INFORMATION: reverse primer for amplifying promoter of
      MODY3 gene

<400> SEQUENCE: 4
gcgtgggttg cgtttgcctg c                                            21

<210> SEQ ID NO 5
<211> LENGTH: 20
```

<212> TYPE: DNA
<213> ORGANISM: Artificial Sequence
<220> FEATURE:
<223> OTHER INFORMATION: forward primer for amplifying exon1 of
     MODY3 gene

<400> SEQUENCE: 5
cgtggccctg tggcagccga                                              20

<210> SEQ ID NO 6
<211> LENGTH: 21
<212> TYPE: DNA
<213> ORGANISM: Artificial Sequence
<220> FEATURE:
<223> OTHER INFORMATION: reverse primer for amplifying exon1 of
     MODY3 gene

<400> SEQUENCE: 6
gggctcgtta ggagctgagg g                                            21

<210> SEQ ID NO 7
<211> LENGTH: 22
<212> TYPE: DNA
<213> ORGANISM: Artificial Sequence
<220> FEATURE:
<223> OTHER INFORMATION: forward primer for amplifying exon2 of
     MODY3 gene

<400> SEQUENCE: 7
cccttgctga gcagatcccg tc                                           22

<210> SEQ ID NO 8
<211> LENGTH: 21
<212> TYPE: DNA
<213> ORGANISM: Artificial Sequence
<220> FEATURE:
<223> OTHER INFORMATION: reverse primer for amplifying exon2 of
     MODY3 gene

<400> SEQUENCE: 8
gggatggtga agcttccagc c                                            21

<210> SEQ ID NO 9
<211> LENGTH: 20
<212> TYPE: DNA
<213> ORGANISM: Artificial Sequence
<220> FEATURE:
<223> OTHER INFORMATION: forward primer for amplifying exon3 of
     MODY3 gene

<400> SEQUENCE: 9
gcaaggtcag gggaatggac                                              20

<210> SEQ ID NO 10
<211> LENGTH: 23
<212> TYPE: DNA
<213> ORGANISM: Artificial Sequence
<220> FEATURE:
<223> OTHER INFORMATION: reverse primer for amplifying exon3 of
     MODY3 gene

<400> SEQUENCE: 10
cgccgttgta cctattgcac tcc                                          23

<210> SEQ ID NO 11
<211> LENGTH: 23
<212> TYPE: DNA

```
<213> ORGANISM: Artificial Sequence
<220> FEATURE:
<223> OTHER INFORMATION: forward primer for amplifying exon4 of
      MODY3 gene

<400> SEQUENCE: 11
ggctcatggg tggctatttc tgc                                              23

<210> SEQ ID NO 12
<211> LENGTH: 23
<212> TYPE: DNA
<213> ORGANISM: Artificial Sequence
<220> FEATURE:
<223> OTHER INFORMATION: reverse primer for amplifying exon4 of
      MODY3 gene

<400> SEQUENCE: 12
cgtgtccctt gtccccacat acc                                              23

<210> SEQ ID NO 13
<211> LENGTH: 22
<212> TYPE: DNA
<213> ORGANISM: Artificial Sequence
<220> FEATURE:
<223> OTHER INFORMATION: forward primer for amplifying exon5 of
      MODY3 gene

<400> SEQUENCE: 13
tgctgaggca ggacactgct tc                                               22

<210> SEQ ID NO 14
<211> LENGTH: 23
<212> TYPE: DNA
<213> ORGANISM: Artificial Sequence
<220> FEATURE:
<223> OTHER INFORMATION: reverse primer for amplifying exon5 of
      MODY3 gene

<400> SEQUENCE: 14
tacaagcaag gacactcacc agc                                              23

<210> SEQ ID NO 15
<211> LENGTH: 21
<212> TYPE: DNA
<213> ORGANISM: Artificial Sequence
<220> FEATURE:
<223> OTHER INFORMATION: forward primer for amplifying exon6 of
      MODY3 gene

<400> SEQUENCE: 15
cccggacaca gcttggcttc c                                                21

<210> SEQ ID NO 16
<211> LENGTH: 23
<212> TYPE: DNA
<213> ORGANISM: Artificial Sequence
<220> FEATURE:
<223> OTHER INFORMATION: reverse primer for amplifying exon6 of
      MODY3 gene

<400> SEQUENCE: 16
atccccacca gcttaccgat gac                                              23

<210> SEQ ID NO 17
<211> LENGTH: 20
<212> TYPE: DNA
<213> ORGANISM: Artificial Sequence
```

```
<220> FEATURE:
<223> OTHER INFORMATION: forward primer for amplifying exon7 of
      MODY3 gene

<400> SEQUENCE: 17
caggcctggc ctccacgcag                                              20

<210> SEQ ID NO 18
<211> LENGTH: 21
<212> TYPE: DNA
<213> ORGANISM: Artificial Sequence
<220> FEATURE:
<223> OTHER INFORMATION: reverse primer for amplifying exon7 of
      MODY3 gene

<400> SEQUENCE: 18
ggggctctgc agctgagcca t                                            21

<210> SEQ ID NO 19
<211> LENGTH: 21
<212> TYPE: DNA
<213> ORGANISM: Artificial Sequence
<220> FEATURE:
<223> OTHER INFORMATION: forward primer for amplifying exon8 and 9 of
      MODY3 gene

<400> SEQUENCE: 19
ggcccagtac acccacacgg g                                            21

<210> SEQ ID NO 20
<211> LENGTH: 21
<212> TYPE: DNA
<213> ORGANISM: Artificial Sequence
<220> FEATURE:
<223> OTHER INFORMATION: reverse primer for amplifying exon8 and 9 of
      MODY3 gene

<400> SEQUENCE: 20
gggcagggac agtaagggag g                                            21

<210> SEQ ID NO 21
<211> LENGTH: 21
<212> TYPE: DNA
<213> ORGANISM: Artificial Sequence
<220> FEATURE:
<223> OTHER INFORMATION: forward primer for amplifying exon10 of
      MODY3 gene

<400> SEQUENCE: 21
gccttgtttg cctctgcagt g                                            21

<210> SEQ ID NO 22
<211> LENGTH: 22
<212> TYPE: DNA
<213> ORGANISM: Artificial Sequence
<220> FEATURE:
<223> OTHER INFORMATION: reverse primer for amplifying exon10 of
      MODY3 gene

<400> SEQUENCE: 22
ggccatctgg gtggagatga ag                                           22

<210> SEQ ID NO 23
<211> LENGTH: 21
<212> TYPE: DNA
<213> ORGANISM: Artificial Sequence
<220> FEATURE:
```

<223> OTHER INFORMATION: modified forward primer for amplifying promoter
      of MODY3 gene

<400> SEQUENCE: 23
ccgtgagcat cctctgccct t                                              21

<210> SEQ ID NO 24
<211> LENGTH: 21
<212> TYPE: DNA
<213> ORGANISM: Artificial Sequence
<220> FEATURE:
<223> OTHER INFORMATION: modified reverse primer for amplifying promoter
      of MODY3 gene

<400> SEQUENCE: 24
accgcgtggg ttgcgtttgc c                                              21

<210> SEQ ID NO 25
<211> LENGTH: 20
<212> TYPE: DNA
<213> ORGANISM: Artificial Sequence
<220> FEATURE:
<223> OTHER INFORMATION: modified forward primer for amplifying exon1 of
      MODY3 gene

<400> SEQUENCE: 25
ccgcgtggcc ctgtggcagc                                                20

<210> SEQ ID NO 26
<211> LENGTH: 21
<212> TYPE: DNA
<213> ORGANISM: Artificial Sequence
<220> FEATURE:
<223> OTHER INFORMATION: modified reverse primer for amplifying exon1 of
      MODY3 gene

<400> SEQUENCE: 26
ctcgttagga gctgaggggg g                                              21

<210> SEQ ID NO 27
<211> LENGTH: 22
<212> TYPE: DNA
<213> ORGANISM: Artificial Sequence
<220> FEATURE:
<223> OTHER INFORMATION: modified forward primer for amplifying exon2 of
      MODY3 gene

<400> SEQUENCE: 27
ttgctgagca gatcccgtcc tt                                             22

<210> SEQ ID NO 28
<211> LENGTH: 21
<212> TYPE: DNA
<213> ORGANISM: Artificial Sequence
<220> FEATURE:
<223> OTHER INFORMATION: modified reverse primer for amplifying exon2 of
      MODY3 gene

<400> SEQUENCE: 28
atggggatgg tgaagcttcc a                                              21

<210> SEQ ID NO 29
<211> LENGTH: 21
<212> TYPE: DNA
<213> ORGANISM: Artificial Sequence
<220> FEATURE:
<223> OTHER INFORMATION: modified forward primer for amplifying exon8 of -continued MODY3 gene

<400> SEQUENCE: 29
ggtggcccag tacacccaca c                                              21

<210> SEQ ID NO 30
<211> LENGTH: 21
<212> TYPE: DNA
<213> ORGANISM: Artificial Sequence
<220> FEATURE:
<223> OTHER INFORMATION: modified reverse primer for amplifying exon8 of
      MODY3 gene

<400> SEQUENCE: 30
cagggacagt aagggagggg g                                              21

<210> SEQ ID NO 31
<211> LENGTH: 434
<212> TYPE: DNA
<213> ORGANISM: Homo sapiens

<400> SEQUENCE: 31
ctcctgtctc agcatgatgc ccctacaagg ttctttcggg ggtgggaccc aacgctgctc     60
tcctgatggc ctccctggct cccagcacct tccatcccag ctgctcaggg cccctcacct    120
gcgcctcccc caccctcccc tctgcccact cccatcgcag gccatagctc cctgtccctc    180
tccgctgcca tgaggcctgc actttgcagg gctgaagtcc aaagttcagt cccttcgcta    240
agcacacgga taaatatgaa ccttggagaa tttcccagc tccaatgtaa acagaacagg     300
caggggccct gattcacggg ccgctgggggc cagggttggg ggttggggggt gcccacaggg  360 cttggctagt ggggttttgg gggggcagtg ggtgcaagga gtttggtttg tgtctgccgg    420
ccggcaggca aacg                                                     434